United States Patent
Stache et al.

(10) Patent No.: US 10,093,826 B2
(45) Date of Patent: Oct. 9, 2018

(54) ALKOXYSILANE-FUNCTIONALIZED ALLOPHANATE-CONTAINING COATING COMPOSITIONS

(71) Applicant: Evonik Degussa GmbH, Essen (DE)

(72) Inventors: Wiebke Stache, Herten (DE); Tobias Unkelhäußer, Dülmen (DE); Emmanouil Spyrou, Schermbeck (DE); Annegret Lilienthal, Dorsten (DE); Ralf Klawikowski, Recklinghausen (DE); Sabine Naumann, Herne (DE); Bartholomäus Buchczik, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/622,204

(22) Filed: Jun. 14, 2017

(65) Prior Publication Data
US 2017/0369736 A1  Dec. 28, 2017

(30) Foreign Application Priority Data
Jun. 27, 2016 (EP) .................................... 16176309

(51) Int. Cl.
| | | |
|---|---|---|
| C07F 7/18 | (2006.01) | |
| C09D 175/04 | (2006.01) | |
| C08G 18/71 | (2006.01) | |
| C08G 18/73 | (2006.01) | |
| C08G 18/75 | (2006.01) | |
| C08G 18/80 | (2006.01) | |
| C08G 18/22 | (2006.01) | |
| C08G 18/24 | (2006.01) | |
| C08G 18/28 | (2006.01) | |
| C08G 18/38 | (2006.01) | |

(52) U.S. Cl.
CPC ............. *C09D 175/04* (2013.01); *C07F 7/18* (2013.01); *C08G 18/222* (2013.01); *C08G 18/246* (2013.01); *C08G 18/282* (2013.01); *C08G 18/3831* (2013.01); *C08G 18/3893* (2013.01); *C08G 18/718* (2013.01); *C08G 18/73* (2013.01); *C08G 18/755* (2013.01); *C08G 18/807* (2013.01); *C08G 18/809* (2013.01)

(58) Field of Classification Search
None
See application file for complete search history.

(56) References Cited

U.S. PATENT DOCUMENTS

| | | | | |
|---|---|---|---|---|
| 3,903,052 A | * | 9/1975 | Wagner | ........... C08G 18/798 528/21 |
| 4,036,813 A | * | 7/1977 | Hardman | ............ C08L 83/04 524/188 |
| 4,650,835 A | * | 3/1987 | Eck | ................... C07F 7/1836 525/440.03 |
| 4,772,672 A | | 9/1988 | Isozaki et al. | |
| 5,220,047 A | * | 6/1993 | Pohl | ..................... C03C 17/30 556/420 |
| 5,516,559 A | | 5/1996 | Roeckrath et al. | |
| 5,990,345 A | * | 11/1999 | Lohmann | .............. C07C 263/04 560/215 |
| 6,319,311 B1 | * | 11/2001 | Katz | .................... C08G 18/289 106/287.11 |
| 6,495,650 B2 | | 12/2002 | Kohlstruk et al. | |
| 6,914,115 B2 | | 7/2005 | Spyrou et al. | |
| 6,960,620 B2 | | 11/2005 | Wenning et al. | |
| 7,060,849 B1 | * | 6/2006 | Childress | ............ C07F 7/1892 556/414 |

(Continued)

FOREIGN PATENT DOCUMENTS

| | | |
|---|---|---|
| CA | 1081389 | 7/1980 |
| DE | 2356768 A1 | 1/1975 |

(Continued)

OTHER PUBLICATIONS

Kozakiewicz et al. "New family of functionalized crosslinkers for heat-curable polyurethane systems—A prelimary study" Progress in Organic Coatings 2011, 72, 120-130 (Year: 2011).*

(Continued)

*Primary Examiner* — Robert S Loewe
(74) *Attorney, Agent, or Firm* — Nexsen Pruet, PLLC; Philip P. McCann

(57) ABSTRACT

The present invention relates to alkoxysilane-functionalized, allophanate-containing coating compositions, to a process for producing them, and to their use. In particular, the alkoxysilane-functionalized, allophanate-containing coating compositions include a) as a binder component, 10-99 wt % of at least one reaction product of i) at least one monourethane i) containing alkoxysilane groups and of the formula 1

$$R_n(OR^1)_{3-n}Si-R^2-NH-(C=O)-OR^3 \qquad \text{formula 1}$$

where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and ii) at least one diisocyanate ii), in a molar ratio of i) to ii) of from 3:1 to 1.5:1, preferably from 2.5:1 to 1.8:1, particularly preferably 2:1; b) 1-90 wt % of at least one other binder component, different from a), preferably a hydroxyl-containing or amino-containing binder component, c) 0-50 wt % of at least one aromatic, aliphatic or cycloaliphatic polyisocyanate having an NCO functionality of at least 2, preferably 2.8 to 6, d) 0-5 wt % of at least one catalyst, where components a)-d) add up to 100 wt %.

20 Claims, No Drawings

(56) References Cited

U.S. PATENT DOCUMENTS

| | | |
|---|---|---|
| 7,307,135 B2 | 12/2007 | Spyrou |
| 7,812,087 B2 | 10/2010 | Ludewig et al. |
| 8,013,099 B2 | 9/2011 | Poppe et al. |
| 8,067,522 B2 | 11/2011 | Ludewig et al. |
| 8,163,390 B2 | 4/2012 | Gruber et al. |
| 8,476,376 B2 | 7/2013 | Grenda et al. |
| 8,524,837 B2 | 9/2013 | Grenda et al. |
| 8,569,440 B2 | 10/2013 | Spyrou et al. |
| 8,674,050 B2 | 3/2014 | Spyrou |
| 8,829,146 B2 | 9/2014 | Spyrou |
| 9,040,622 B2 * | 5/2015 | Boghossian .......... B32B 15/02 524/589 |
| 9,096,774 B2 | 8/2015 | Grenda et al. |
| 9,115,293 B2 | 8/2015 | Lomoelder et al. |
| 9,175,126 B2 | 11/2015 | Albrecht et al. |
| 2002/0016486 A1 * | 2/2002 | Pinske .................. C07F 7/083 556/411 |
| 2004/0077778 A1 * | 4/2004 | Hazan ................. C08G 18/289 524/589 |
| 2005/0239956 A1 | 10/2005 | Spyrou et al. |
| 2005/0239992 A1 | 10/2005 | Spyrou et al. |
| 2007/0266897 A1 | 11/2007 | Spyrou |
| 2007/0282089 A1 | 12/2007 | Spyrou |
| 2008/0139753 A1 | 6/2008 | Spyrou et al. |
| 2008/0171816 A1 | 7/2008 | Spyrou et al. |
| 2008/0214728 A1 | 9/2008 | Spyrou et al. |
| 2008/0265201 A1 | 10/2008 | Spyrou et al. |
| 2008/0269415 A1 | 10/2008 | Spyrou et al. |
| 2009/0286901 A1 * | 11/2009 | Vijverberg .......... C09C 1/3081 523/206 |
| 2009/0326146 A1 | 12/2009 | Sepeur et al. |
| 2010/0010113 A1 | 1/2010 | Schwalm et al. |
| 2010/0092686 A1 | 4/2010 | Laryea et al. |
| 2010/0179273 A1 | 7/2010 | Spyrou et al. |
| 2010/0227942 A1 | 9/2010 | Spyrou et al. |
| 2010/0247929 A1 | 9/2010 | Oertli et al. |
| 2011/0082254 A1 | 4/2011 | Sepeur et al. |
| 2012/0029143 A1 | 2/2012 | Sepeur et al. |
| 2012/0077932 A1 | 3/2012 | Pfeffer et al. |
| 2013/0041103 A1 | 2/2013 | Grenda et al. |
| 2013/0244043 A1 | 9/2013 | Lomoelder et al. |
| 2013/0245194 A1 * | 9/2013 | Huang ................. C08G 18/10 524/588 |
| 2015/0126678 A1 * | 5/2015 | Kramer .............. C08G 18/4866 524/590 |
| 2015/0191625 A1 | 7/2015 | Lomoelder et al. |
| 2015/0225337 A1 | 8/2015 | Lomoelder et al. |
| 2015/0232609 A1 | 8/2015 | Spyrou et al. |
| 2015/0266992 A1 | 9/2015 | Spyrou et al. |
| 2015/0274760 A1 | 10/2015 | Spyrou et al. |
| 2015/0329752 A1 | 11/2015 | Albrecht et al. |
| 2016/0115351 A1 * | 4/2016 | Iezzi ................. C08G 18/3821 524/588 |
| 2016/0200745 A1 * | 7/2016 | Stanjek ................. C07F 7/1892 556/420 |
| 2016/0251472 A1 | 9/2016 | Spyrou et al. |

FOREIGN PATENT DOCUMENTS

| | | | |
|---|---|---|---|
| DE | 102005041953 A1 | 3/2007 | |
| DE | 102005041954 A1 | 3/2007 | |
| DE | 102005045228 A1 | 4/2007 | |
| EP | 0140186 A1 | 5/1985 | |
| EP | 2676982 A1 | 12/2013 | |
| EP | 3162807 A1 * | 5/2017 | ............... C07F 7/18 |
| PL | 211785 * | 1/2010 | ............. C08L 75/04 |
| WO | 9211328 A1 | 7/1992 | |
| WO | 9315849 A1 | 8/1993 | |
| WO | 2005105879 A1 | 11/2005 | |
| WO | 2005105880 A1 | 11/2005 | |
| WO | 2006040226 A1 | 4/2006 | |
| WO | 2008028769 A1 | 3/2008 | |
| WO | 2008043722 A1 | 4/2008 | |
| WO | 2008068068 A1 | 6/2008 | |
| WO | 2008068073 A1 | 6/2008 | |
| WO | 2008131715 A1 | 11/2008 | |
| WO | 2008138855 A1 | 11/2008 | |

OTHER PUBLICATIONS

European Search Report dated Sep. 12, 2016 in EP 16 17 6309 (1 page).

Stache et al., U.S. Appl. No. 15/614,763, filed Jun. 6, 2017.

Stache et al., U.S. Appl. No. 15/619,897, filed Jun. 12, 2017.

Stache et al., U.S. Appl. No. 15/622,159, filed Jun. 14, 2017.

* cited by examiner

ALKOXYSILANE-FUNCTIONALIZED ALLOPHANATE-CONTAINING COATING COMPOSITIONS

This application claims the benefit of European Application No. 16176309.9 filed on Jun. 27, 2016, the disclosure of which is expressly incorporated herein by reference.

BACKGROUND

The present invention relates to alkoxysilane-functionalized, allophanate-containing coating compositions, to a process for producing them, and to their use.

Polyurethanes have been established for many decades as high-value components for paint, adhesive, sealant and plastics systems. It is possible here for additional alkoxysilane groups to play an important role, for example with regard to network density, chemical resistance and scratch resistance, primarily through the formation of siloxane and polysiloxane structures.

Molecules both possessing alkoxysilane groups and having isocyanate groups offer the option of introducing the functionalities that are the resulting reaction products, siloxanes and polyurethane groups, by means of one component. Such substances have long been in use, for example in the form of isocyanatoalkyltrialkoxysilanes.

Alkoxysilane-terminated polyurethanes prepared from isocyanatoalkyltrialkoxysilanes and alcohols are likewise known and are used, for example, for producing highly crosslinked, hard coating materials (e.g. EP 2676982 A1). The alkoxysilane-containing coating materials described in EP 2676982 A1, however, are disadvantageous in having only short potlives.

Allophanate-containing binders are long-established systems. Alkoxysilane-functionalized allophanates as well are known. It is appropriate here to distinguish between a variety of types, which are set out below, but which correspond neither in structure nor in application to the alkoxysilane-functionalized allophanate present in the alkoxysilane-functionalized, allophanate-containing coating composition of the invention.

Accordingly the allophanates III (1) described in WO 2008/043722 A1 are obtained by reaction of NCO-terminated allophanate-containing polyurethanes I (1) with isocyanate-reactive alkoxysilanes II (1) (e.g. aminoalkyltrialkoxysilane). The allophanate groups here are therefore located in the centre of the polyurethane chain, and the alkoxysilane function is attached via the terminal isocyanate group, in the form of a urea function (structure III (1), equation 1).

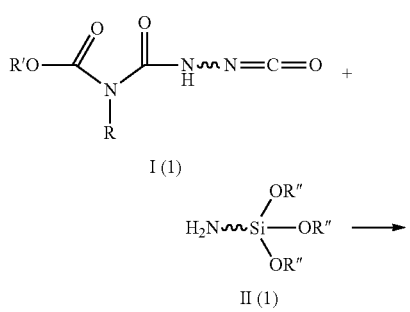

(Equation 1)

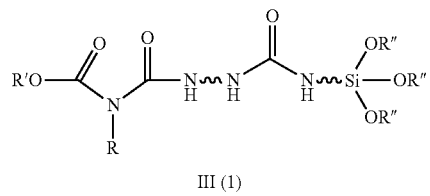

III (1)

DE 102005041953 A1 describes the reaction of a polyol I (2) having a mean molecular weight of 3000-20 000 g/mol with an excess of isocyanatopropyltrimethoxysilane II (2) so as to result, after polyurethane formation III (2), in the formation of an allophanate IV (2) having two alkoxysilane functions per allophanate unit.

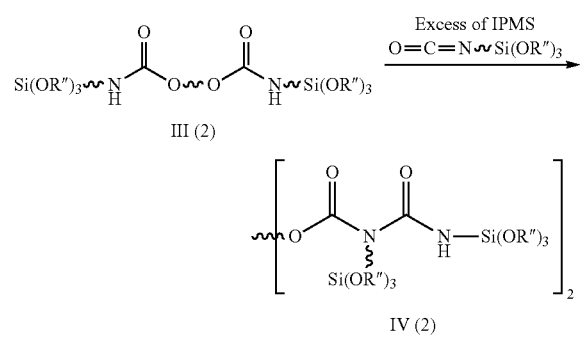

(Equation 2)

In DE 102005041954 A1, a polyurethane I (3) is admixed with isocyanatopropyltrimethoxysilane II (3) and the mixture is heated until allophanate structures are formed. In this case, the alkoxysilane group is built on the terminal nitrogen of the allophanate group III (3) (equation 3).

(Equation 3)

J. Kozakiewicz et al. published, in *Progress in Organic Coatings* 72 (2011) 120-130, the reaction of isocyanatopropyltrimethoxysilane I (4) with methanol to form the corresponding urethane II (4) and subsequently with hexamethylene diisocyanate trimer III (4). In the resultant, highly viscous allophanate IV (4), the alkoxysilane function is pendent on the tertiary, central amine of the allophanate group (equation 4).

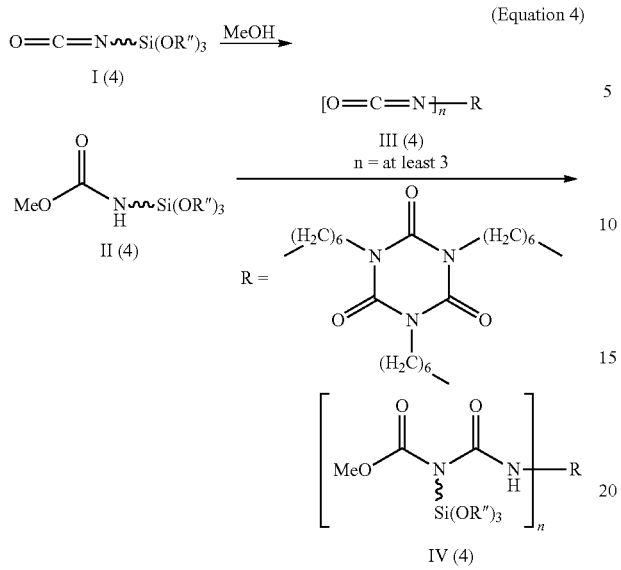

(Equation 4)

In the application described, the allophanate function serves as blocking agent for the hexamethylene diisocyanate trimer used as crosslinker for hydroxy-functionalized polyester polyols.

Even today there is a need for new silane-containing coating compositions which possess specific properties.

The alkoxysilane-containing binders described in EP 2676982 A1 are disadvantageous in having only short pot-lives.

SUMMARY

The object of this invention is to provide access to new silane-containing coating compositions which are suitable for the development of highly crosslinked, hard coatings and are distinguished by extended potlife.

This object is achieved by alkoxysilane-functionalized, allophanate-containing coating compositions in accordance with the present invention.

Surprisingly it has been found that the alkoxysilane-functionalized and allophanate-containing coating compositions of the invention are suitable for application as paint, adhesive or sealant. More particularly, the alkoxysilane-functionalized and allophanate-containing coating compositions of the invention can be used for developing highly crosslinked, particularly hard coatings with good adhesion. The alkoxysilane-functionalized and allophanate-containing coating compositions of the invention, comprising the alkoxysilane-functionalized and allophanate-containing binder components a) of the invention, are notable, moreover, for a long potlife.

DETAILED DESCRIPTION

A subject of the invention are alkoxysilane-functionalized and allophanate-containing coating compositions comprising a) as a binder component, 10-99 wt % of at least one reaction product of
  i) at least one, preferably one, monourethane i) containing alkoxysilane groups and of the formula 1

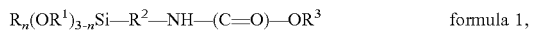

formula 1, where R, $R^1$, $R^2$ and $R^3$ are each independently hydrocarbyl radicals having 1-8 carbon atoms, which may be linear, branched or cyclic, or else may be integrated together to form a cyclic system, and n is 0-2,
and ii) at least one diisocyanate ii),
in a molar ratio of i) to ii) of from 3:1 to 1.5:1, preferably from 2.5:1 to 1.8:1, particularly preferably 2:1;

b) 1-90 wt % of at least one other binder component, different from a), preferably a hydroxyl-containing or amino-containing binder component, c) 0-50 wt % of at least one aromatic, aliphatic or cycloaliphatic polyisocyanate having an NCO functionality of at least 2, preferably 2.8 to 6, d) 0-5 wt % of at least one catalyst,
where components a)-d) add up to 100 wt %, e) optionally auxiliaries and/or additives, f) optionally solvents.

The allophanate-containing coating compositions of the invention are coating compositions comprising at least one reaction product of at least one monourethane with at least one diisocyanate. Such reaction products, as is evident from the reaction of at least one monourethane with at least one diisocyanate, comprise adducts having on average one or two allophanate units, since the diisocyanate may be consumed partially or completely by reaction with one or two monourethanes. Preferably, however, the reaction product of the invention has two allophanate units.

The reaction product is obtained by reaction of at least one monourethane with at least one diisocyanate in the stated stoichiometry. The reaction product is preferably obtained by reaction of a monourethane with at least one diisocyanate in the stated stoichiometry. With further preference the reaction product is obtained by reaction of a monourethane or a diisocyanate in the stated stoichiometry. A monourethane or a diisocyanate refers in each case, in particular, to the respective monourethane or the respective diisocyanate of an empirical formula.

"A" monourethane and "a" diisocyanate refer in each case here, in particular, to the respective monourethane and diisocyanate of an empirical formula.

Under the term "binder components" it is possible with preference to understand binders and crosslinkers, more preferably binders.

A preferred subject of the invention are not only coating compositions comprising the stated components a)-f), but also coating compositions consisting of said components. A preferred subject of the invention are therefore alkoxysilane-functionalized, allophanate-containing coating compositions consisting of a) as a binder component, 10-99 wt % of at least one reaction product of
  i) at least one, preferably one, monourethane i) containing alkoxysilane groups and of the formula 1

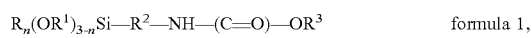

formula 1, where R, $R^1$, $R^2$ and $R^3$ are each independently hydrocarbyl radicals having 1-8 carbon atoms, which may be linear, branched or cyclic, or else may be integrated together to form a cyclic system, and n is 0-2,
and ii) at least one diisocyanate ii),
in a molar ratio of i) to ii) of from 3:1 to 1.5:1, preferably from 2.5:1 to 1.8:1, particularly preferably 2:1;

b) 1-90 wt % of at least one other binder component, different from a), preferably a hydroxyl-containing or amino-containing binder component, c) 0-50 wt % of at least one aromatic, aliphatic or cycloaliphatic polyisocyanate having an NCO functionality of at least 2, preferably 2.8 to 6, d) 0-5 wt % of at least one catalyst, where components a)-d) add up to 100 wt %, e) optionally auxiliaries and/or additives, f) optionally solvents.

In one preferred embodiment, the coating composition of the invention is a non-aqueous coating composition. In one particularly preferred embodiment, the term "non-aqueous", as used herein, means that the coating composition of the invention, based on the sum of the components a)-f), has a water fraction of not more than 3 weight percent, preferably not more than 1 weight percent. In one particularly preferred embodiment, the coating composition of the invention is free from water.

Component a) is included in the coating composition of the invention at 10 to 99 wt %, preferably at 10 to 70 wt %, based on the sum of the components a), b), optionally c) and d).

Preferably R, $R^1$, $R^2$ and $R^3$ at the same time or mutually independently are methyl, ethyl, n-propyl, isopropyl, n-butyl, sec-butyl or tert-butyl.

Preferably, n=0.

$R^1$ and $R^3$ are preferably, simultaneously or mutually independently, methyl or ethyl.

$R^2$ is preferably methyl or propyl.

Preferred compounds are those where n is 0, $R^1$ and $R^3$ are at the same time or each independently methyl or ethyl, and $R^2$ is at the same time or mutually independently methyl or propyl.

Preferably, $R^3=R^1$.

Preference is given to compounds where n is 0 and $R^2$ is methyl or propyl, and $R^1$ is methyl or ethyl and $R^3=R^1$.

Very particular preference is given to the compound where n is 0, $R^1$ and $R^3$ are methyl and $R^2$ is propyl, N-trimethoxysilylpropyl methylcarbamate.

After reaction of the monourethane i) containing alkoxysilane groups with the diisocyanate ii) in accordance with the invention, the NCO content of the end product is preferably <3 wt %, more preferably <1 wt %, very preferably <0.2 wt %.

The diisocyanates ii) used in accordance with the invention may consist of any desired aromatic, aliphatic, cycloaliphatic and/or (cyclo)aliphatic diisocyanates. In one preferred embodiment, the term "(cyclo)aliphatic diisocyanate", as used herein, is understood to mean that in one molecule there are, simultaneously, NCO groups bonded to a ring and NCO groups bonded to an aliphatic radical, as is the case, for example, for isophorone diisocyanate. In one preferred embodiment the terms "cycloaliphatic diisocyanate" as used herein is understood to refer to a diisocyanate which only has NCO groups bonded directly on the cycloaliphatic ring, for example diisocyanatodicyclohexylmethane (H12MDI).

Suitable aromatic diisocyanates ii) are in principle all known aromatic compounds. Particularly suitable are phenylene 1,3- and 1,4-diisocyanate, naphthylene 1,5-diisocyanate, tolylene 2,6-diisocyanate (2,6-TDI), tolylene 2,4-diisocyanate (2,4-TDI), diphenylmethane 2,4'-diisocyanate (2,4'-MDI), diphenylmethane 4,4'-diisocyanate (4,4'-MDI), the mixtures of monomeric diphenylmethane diisocyanates (MDI) and oligomeric diphenylmethane diisocyanates (polymer MDI), xylylene diisocyanate (MXDI) and tetramethylxylylene diisocyanate (TMXDI).

Suitable aliphatic diisocyanates ii) possess advantageously 3 to 16 carbon atoms, preferably 4 to 12 carbon atoms, in the linear and/or branched alkylene radical.

Suitable cycloaliphatic or (cyclo)aliphatic diisocyanates ii) advantageously have 4 to 18 carbon atoms, preferably 6 to 15 carbon atoms, in the cycloalkylene radical. (Cyclo)aliphatic diisocyanates are well understood in the art as referring to both cyclically and aliphatically attached NCO groups, as is the case with isophorone diisocyanate for example.

By contrast, cycloaliphatic diisocyanates are diisocyanates where only NCO groups are directly attached to the cycloaliphatic ring, e.g. H12MDI.

Examples are cyclohexane diisocyanate, methylcyclohexane diisocyanate, ethylcyclohexane diisocyanate, propylcyclohexane diisocyanate, methyldiethylcyclohexane diisocyanate, propane diisocyanate, butane diisocyanate, pentane diisocyanate, hexane diisocyanate, heptane diisocyanate, octane diisocyanate, nonane diisocyanate, nonane triisocyanate, such as 4-isocyanatomethyl-1,8-octane diisocyanate (TIN), decane di- and triisocyanate, undecane di- and triisocyanate, dodecane di- and triisocyanates. Likewise suitable are 4-methylcyclohexane 1,3-diisocyanate, 2-butyl-2-ethylpentamethylene diisocyanate, 3(4)-isocyanatomethyl-1-methylcyclohexyl isocyanate, 2-isocyanatopropylcyclohexyl isocyanate, diisocyanatodicyclohexylmethane (H12MDI), 1,4-diisocyanato-4-methylpentane.

Preferred diisocyanates ii) are isophorone diisocyanate (IPDI), hexamethylene diisocyanate (HDI), dicyclohexylmethane 2,2'-diisocyanate (2,2'-H12MDI), dicyclohexylmethane 2,4'-diisocyanate (2,4'-H12MDI), dicyclohexylmethane 4,4'-diisocyanate (4,4'-H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), xylylene diisocyanate (MXDI), individually or in a mixture.

Particular preference is given to isophorone diisocyanate (IPDI), hexamethylene diisocyanate (HDI), 4,4'-diisocyanatodicyclohexylmethane, 2,4'-diisocyanatodicyclohexylmethane, 2,2'-diisocyanatodicyclohexylmethane, alone or in mixtures of the isomers (H12MDI), 2-methylpentane diisocyanate (MPDI), 2,2,4-trimethylhexamethylene diisocyanate, 2,4,4-trimethylhexamethylene diisocyanate and mixtures thereof (TMDI), norbornane diisocyanate (NBDI), MXDI, alone or in a mixture.

Very particular preference is given to using IPDI, HDI, TMDI, MXDI and H12MDI, alone or in a mixture.

In one particularly preferred embodiment the diisocyanate ii) comprises IPDI and/or 4,4'-H12MDI and/or HDI and/or a mixture of 2,2,4-TMDI and 2,4,4-TMDI.

It will be appreciated that it is also possible to use mixtures of diisocyanates ii).

The allophanates a) are generally prepared solventlessly or using non-protic solvents, and the reaction may take place batchwise or continuously. The reaction is conducted in suitable equipment, for example stirred tanks, extruders, static mixers, kneading chambers. The reaction can be conducted at room temperature, i.e. at temperatures in the range from 15-40° C., more particularly in the range of 15-25° C. Preferably, however, higher temperatures are used, in the 80 to 220° C. range, more particularly in the range from 80 to 120° C. The reaction is conducted with exclusion of water. Preference is given to conducting the reaction solventlessly.

To accelerate the reaction, it is possible advantageously to use catalysts C) known in urethane chemistry, examples being organometallic compounds, such as tin or zinc compounds, salts, for example Zn(II) chloride, and/or bases. Suitable for example are carboxylates of Sn, Bi, Zn and other metals, for example dibutyltin dilaurate, tin octoate, zinc ethylhexanoate, bismuth neodecanoate, tertiary amines such as, for example, 1,4-diazabicyclo[2.2.2]octane (DABCO), 1,8-diazabicyclo[5.4.0]undec-7-ene (DBU), 1,5-diazabicyclo[4.3.0]non-5-ene (DBN), triethylamine, amidine and guanidine, and also quaternary ammonium salts, preferably tetraalkylammonium salts, and/or quaternary phosphonium salts.

The coating composition of the invention comprises as component b) at least one other binder component different from a). Suitable in principle as binders are all kinds of binders known to the skilled person, including, for example, binders which are thermoplastic, in other words not cross-linkable, which customarily have an average molecular weight>10 000 g/mol. Preferred binders, however, are those which possess reactive functional groups having acidic hydrogen atoms, examples being hydroxyl or primary or secondary amine groups. Suitable binders of the cited type have for example at least one, but preferably two or more, hydroxyl group(s). Further suitable functional groups of the binder are alkoxysilane functionalities, for example.

As binder component b) having functional groups, preference is given to using hydroxyl-containing polyesters, polyethers, polyacrylates, polycarbonates and polyurethanes having an OH number of 20 to 500 mg KOH/g and a mean molar mass of 250 to 6000 g/mol. Particular preference in the context of the present invention is given to using hydroxyl-containing polyesters or polyacrylates having an OH number of 50 to 250 mg KOH/g and a mean molecular weight of 500 to 6000 g/mol as binder components. The hydroxyl number (OH number, OHN) is determined in accordance with DIN 53240-2. This method comprises reacting the sample with acetic anhydride in the presence of 4-dimethylaminopyridine as catalyst to acetylate the hydroxyl groups. This affords one molecule of acetic acid per hydroxyl group while the subsequent hydrolysis of the excess acetic anhydride yields two molecules of acetic acid. The consumption of acetic acid is determined by titrimetry from the difference between the main value and a blank value to be carried out in parallel. The molecular weight is determined by means of gel permeation chromatography (GPC). The samples are characterized in tetrahydrofuran as eluent in accordance with DIN 55672-1.

Hydroxyl-containing (meth)acrylic copolymers which may be used as binder component b) may be resins having a monomer composition of the kind described, for example, in WO 93/15849 A1 (page 8, line 25 to page 10, line 5). In that case the acid number of the (meth)acrylic copolymer, to be set through proportional use of (meth)acrylic acid as monomer, ought to be 0 to 30, preferably 0 to 15 mg KOH/g. The number-average molar weight (determined by gel permeation chromatography against a polystyrene standard) of the (meth)acrylic copolymer is preferably 2000 to 20 000 g/mol; the glass transition temperature is preferably −40° C. to +60° C. The hydroxyl content of the (meth)acrylic copolymers for use in accordance with the invention, to be set through proportional use of hydroxyalkyl (meth)acrylates, is preferably 20 to 500 mg KOH/g, more preferably 50 to 250 mg KOH/g.

Polyester polyols suitable as binder component b) in accordance with the invention are resins having a monomer composition composed of dicarboxylic and polycarboxylic acids and of diols and polyols, as described in WO 93/15849 A1. Also employable as polyester polyols are polyaddition products of caprolactone onto low molecular weight di- and triols as are available under the trade name CAPA® (Perstorp) for example. The arithmetically determined number-average molar weight is preferably 500 to 5000 g/mol, more preferably 800 to 3000 g/mol; the average functionality is preferably 2.0 to 4.0, more preferably 2.0 to 3.5.

As urethane- and ester-group-containing polyols which may be used in accordance with the invention as binder component b), those employed include in principle those of the kind as described in EP 140 186 A1. Preference is given to urethane- and ester-group-containing polyols which are prepared using HDI, IPDI, trimethylhexamethylene diisocyanate (TMDI) or dicyclohexylmethane diisocyanate (H12MDI). The number-average molar weight is preferably 500-5000 g/mol; the average functionality lies more particularly in the range of 2.0-3.5.

Trialkoxysilane-functional binders as well are suitable for use as component b). Such resins may be obtained by copolymerization of acrylate or methacrylate monomers with acryloyl- or methacryloyl-functional alkyltrialkoxysilane derivatives (for example Dynasylan® MEMO from Evonik Industries AG) as are described, for example, in WO 92/11328. An alternative synthesis comprises derivatization of hydroxyl-containing polyethers, polyesters, polycarbonate diols or polyacrylates with isocyanatopropyltrialkoxysilane as is described, for example, in Examples 3 and 4 of WO2008/131715. Also useful are amino-containing binders, for example aminopropyltrimethoxysilane (e.g. Dynasylan AMMO from Evonik Industries AG), aminopropyltriethoxysilane, aminomethyltrimethoxysilane or aminomethyltriethoxysilane.

It will be appreciated that it is also possible to employ mixtures of the binder components b) described hereinabove.

Particularly preferred binder components b) are hydroxyl-containing polyesters and polyacrylates, alone or in a mixture.

The proportion of the binder component b) in the binder of the invention is preferably 1 to 90 weight percent, based on the sum of the components a), b) and optionally c) and d), preferably 20 to 60 weight percent.

Component c)

The polyisocyanates c) used in accordance with the invention may consist of any desired aromatic, aliphatic, cycloaliphatic and/or (cyclo)aliphatic polyisocyanates.

Suitable aromatic polyisocyanates c) are in principle any known aromatic compounds. Particularly suitable are phenylene 1,3- and 1,4-diisocyanate, naphthylene 1,5-diisocyanate, tolylene 2,6-diisocyanate (2,6-TDI), tolylene 2,4-diisocyanate (2,4-TDI), diphenylmethane 2,4'-diisocyanate (2,4'-MDI), diphenylmethane 4,4'-diisocyanate (4,4'-MDI), the mixtures of monomeric diphenylmethane diisocyanates (MDI) and oligomeric diphenylmethane diisocyanates (polymer MDI), xylylene diisocyanate (MXDI) and tetramethylxylylene diisocyanate (TMXDI).

The aliphatic or cycloaliphatic polyisocyanate c) used as crosslinker component c) comprises at least one aliphatic and/or cycloaliphatic polyisocyanate having an NCO functionality of at least 2, preferably 2 to 6, more preferably from 2.8 to 6, most preferably 2 to 4. The term "NCO functionality" as used herein refers to the number of reactive NCO substituents possessed on average by the molecule in question, preferably the crosslinker component c).

The polyisocyanate c) used in accordance with the invention as component c) of the invention may be any aliphatic, cycloaliphatic and/or (cyclo)aliphatic diisocyanate. (Cyclo) aliphatic diisocyanates are well understood in the art as referring to both cyclically and aliphatically attached NCO groups, as is the case with isophorone diisocyanate for example. By contrast, cycloaliphatic diisocyanates are diisocyanates where only NCO groups are directly attached to the cycloaliphatic ring, e.g. H12MDI.

Aliphatic polyisocyanates suitable for use as component c) of the invention include a linear or branched alkylene radical having preferably 3 to 16 carbon atoms, more preferably 4 to 12 carbon atoms. Suitable cycloaliphatic or (cyclo)aliphatic polyisocyanates c) include a cycloalkylene radical having preferably 4 to 18 carbon atoms, more preferably 6 to 15 carbon atoms. Examples of suitable di- or polyisocyanates include cyclohexane diisocyanate, methylcyclohexane diisocyanate, ethylcyclohexane diisocyanate, propylcyclohexane diisocyanate, methyldiethylcyclohexane diisocyanate, propane diisocyanate, butane diisocyanate, pentane diisocyanate, hexane diisocyanate, heptane diisocyanate, octane diisocyanate, nonane diisocyanate, nonane triisocyanate, such as 4-isocyanatomethyl-1,8-octane diisocyanate (TIN), decane di- and triisocyanate, undecane di- and triisocyanate, dodecane di- and triisocyanates. Likewise suitable are 4-methylcyclohexane 1,3-diisocyanate, 2-butyl-2-ethylpentamethylene diisocyanate, 3(4)-isocyanatomethyl-1-methylcyclohexyl isocyanate, 2-isocyanatopropylcyclohexyl isocyanate, 2,4'-methylenebis(cyclohexyl) diisocyanate and/or 1,4-diisocyanato-4-methylpentane.

The polyisocyanate used as component c) of the invention is preferably selected from isophorone diisocyanate (IPDI), hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-dicyclohexylmethane diisocyanate (4,4'-H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), xylylene diisocyanate (MXDI), used individually or as mixtures thereof.

The polyisocyanate used as component c) of the invention is with particular preference selected from the group encompassing isophorone diisocyanate hexamethylene diisocyanate (HDI), diisocyanatodicyclohexylmethane (H12MDI), 2-methylpentane diisocyanate (MPDI), 2,2,4-trimethylhexamethylene diisocyanate/2,4,4-trimethylhexamethylene diisocyanate (TMDI), norbornane diisocyanate (NBDI). Particular preference is given to IPDI, HDI, TMDI and/or H12MDI, with IPDI, H12MDI and/or HDI representing the most preferred polyisocyanates.

Also used with preference as component c) of the invention are polyisocyanates which can be prepared from the stated polyisocyanates or mixtures thereof by linking by means of urethane, allophanate, urea, biuret, uretdione, amide, isocyanurate, carbodiimide, uretonimine, oxadiazinetrione or iminooxadiazinedione structures. Such polyisocyanates are commercially available.

Particularly preferred as component c) of the invention are isocyanurates, especially isocyanurates of IPDI and/or HDI, e.g. VESTANAT HT 2500 L and VESTANAT T 1890.

Polyisocyanates of this kind can optionally additionally be chain-extended or branched with di- or polyfunctional H acidic components, for example di- or polyols and/or di- or polyamines.

Particularly preferred for use as components c) of the invention are isocyanurates freed from residual monomers by distillative removal, to give a polyisocyanate residual monomer content of <0.5 wt %.

For the purposes of the present invention, any desired mixtures of the above-described diisocyanates and/or polyisocyanates may be used.

Component c), if present, is included in the coating composition of the invention at 5 to 50 weight percent, preferably 15 to 40 weight percent, based on the sum of the components a), b), optionally c) and d).

Catalyst d) is included in the coating composition of the invention, in one preferred embodiment, in an amount of 0.1 up to 5 weight percent, preferably 0.2 to 3 weight percent, based on the sum of the components a), b), optionally c) and d).

Catalysts d) used may be organic carboxylic acids. Examples of suitable carboxylic acids are, in particular, salicylic acid, benzoic acid, citric acid, phthalic acid, terephthalic acid, isophthalic acid, dodecanoic acid, 1,12-dodecanedioic acid and/or ascorbic acid. Preference is given to using salicylic acid, citric acid or benzoic acid, and mixtures of the stated carboxylic acids may also be employed.

Catalysts d) which may be used are also quaternary ammonium salts alone or in mixtures, preferably tetraalkylammonium salts and/or quaternary phosphonium salts, with halogens, hydroxides, alkoxides or organic or inorganic acid anions as counterion. Examples of these are: tetramethyl ammonium formate, tetramethylammonium acetate, tetramethylammonium propionate, tetramethylammonium butyrate, tetramethylammonium benzoate, tetraethylammonium formate, tetraethylammonium acetate, tetraethylammonium propionate, tetraethylammonium butyrate, tetraethylammonium benzoate, tetrapropylammonium formate, tetrapropylammonium acetate, tetrapropylammonium propionate, tetrapropylammonium butyrate, tetrapropylammonium benzoate, tetrabutylammonium formate, tetrabutylammonium acetate, tetrabutylammonium propionate, tetrabutylammonium butyrate and tetrabutylammonium benzoate, and tetrabutylphosphonium acetate, tetrabutylphosphonium formate and ethyltriphenylphosphonium acetate, tetrabutylphosphonium benzotriazolate, tetraphenylphosphonium phenolate and trihexyltetradecylphosphonium decanoate, methyltributylammonium hydroxide, methyltriethylammonium hydroxide, tetramethyl ammonium hydroxide, tetraethylammonium hydroxide, tetrapropylammonium hydroxide, tetrabutylammonium hydroxide, tetrapentylammonium hydroxide, tetrahexylammonium hydroxide, tetraoctylammonium hydroxide, tetradecylammonium hydroxide, tetradecyltrihexylammonium hydroxide, tetraoctadecylammonium hydroxide, benzyltrimethylammonium hydroxide, benzyltriethylammonium hydroxide, trimethylphenylammonium hydroxide, triethylmethylammonium hydroxide, trimethylvinylammonium hydroxide, methyltributylammonium methoxide, methyltriethylammonium methoxide, tetramethylammonium methoxide, tetraethylammonium methoxide, tetrapropylammonium methoxide, tetrabutylammonium methoxide, tetrapentylammonium methoxide, tetrahexylammonium methoxide, tetraoctylammonium methoxide, tetradecylammonium methoxide, tetradecyltrihexylammonium methoxide, tetraoctadecylammonium methoxide, benzyltrimethylammonium methoxide, benzyltriethylammonium methoxide, trimethylphenylammonium methoxide, triethylmethylammonium methoxide, trimethylvinylammonium methoxide, methyltributylammonium ethoxide, methyltriethylammonium ethoxide, tetramethylammonium ethoxide, tetraethylammonium ethoxide, tetrapropylammonium ethoxide, tetrabutyl ammonium ethoxide, tetrapentylammonium ethoxide, tetrahexylammonium ethoxide, tetraoctylammonium methoxide, tetradecylammonium ethoxide, tetradecyltrihexylammonium ethoxide, tetraoctadecylammonium ethoxide, benzyltrimethylammonium ethoxide, benzyltriethylammonium ethoxide, trimethylphenylammonium ethoxide, triethylmethylammonium ethoxide, trimethylvinylammonium ethoxide, methyltributylammonium benzylate, methyltriethylammonium benzylate, tetramethylammonium benzylate, tetraethylammonium benzylate, tetrapropylammonium benzylate, tetrabutylammonium benzylate, tetrapentylammonium benzylate, tetrahexylammonium benzylate, tetraoctylammonium benzylate, tetradecylammonium benzylate, tetradecyltrihexyl ammonium benzylate, tetraoctadecylammonium benzylate, benzyltrimethylammonium benzylate, benzyltriethylammonium benzylate, trimethylphenylammonium benzylate, triethylmethylammonium benzylate, trimethylvinylammonium benzylate, tetramethylammonium fluoride, tetraethyl ammonium fluoride, tetrabutylammonium fluoride, tetraoctylammonium fluoride, benzyltrimethylammonium fluoride, tetrabutylphosphonium hydroxide, tetrabutylphosphonium fluoride, tetrabutylammonium chloride, tetrabutylammonium bromide, tetrabutylammonium iodide, tetraethylammonium chloride, tetraethylammonium bromide, tetraethylammonium iodide, tetramethyl ammonium chloride, tetramethylammonium bromide, tetramethylammonium iodide, benzyltrimethylammonium chloride, benzyltriethylammonium chloride, benzyltripropylammonium chloride, benzyltributylammonium chloride, methyltributylammonium chloride, methyltripropylammonium chloride, methyltriethylammonium chloride, methyltriphenylammonium chloride, phenyltrimethylammonium chloride, benzyltrimethylammonium bromide, benzyltriethylammonium bromide, benzyltripropylammonium bromide, benzyltributylammonium bromide, methyltributyl ammonium bromide, methyltripropylammonium bromide, methyltriethylammonium bromide, methyltriphenylammonium bromide, phenyltrimethylammonium bromide, benzyltrimethylammonium iodide, benzyltriethylammonium iodide, benzyltripropylammonium iodide, benzyltributylammonium iodide, methyltributylammonium iodide, methyltripropylammonium iodide, methyltriethylammonium iodide, methyltriphenylammonium iodide and phenyltrimethylammonium iodide, methyltributylammonium hydroxide, methyltriethylammonium hydroxide, tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraoctylammonium hydroxide, tetradecylammonium hydroxide, tetradecyltrihexylammonium hydroxide, tetraoctadecylammonium hydroxide, benzyltrimethylammonium hydroxide, benzyltriethylammonium hydroxide, trimethylphenylammonium hydroxide, triethylmethylammonium hydroxide, trimethylvinylammonium hydroxide, tetramethylammonium fluoride, tetraethylammonium fluoride, tetrabutylammonium fluoride, tetraoctylammonium fluoride and benzyltrimethylammonium fluoride. These catalysts may be added alone or in mixtures. Preference is given to using tetraethylammonium benzoate and tetrabutylammonium hydroxide.

As catalyst d) it is also possible to use metal complexes with chelate ligands. The chelate ligands are organic compounds having at least two functional groups which are able to coordinate to metal atoms or metal ions. Use may be made, for example, of the aluminium- and zirconium-chelate complexes, as described in U.S. Pat. No. 4,772,672 A, for example, as catalyst. Preferred metal chelates are chelate based on zinc, lithium, tin, aluminium, zirconium, titanium and/or boron, for example aluminium ethyl acetoacetate, zirconium ethyl acetoacetate, zinc acetylacetonate, lithium acetylacetonate and tin acetylacetonate, alone or in mixtures. Preference is given to using zinc acetylacetonate.

Useful catalysts d) are also quaternary ammonium acetylacetonates or quaternary phosphonium acetylacetonates.

Examples of such catalysts are tetramethylammonium acetylacetonate, tetraethylammonium acetylacetonate, tetrapropylammonium acetylacetonate, tetrabutylammonium acetylacetonate, benzyltrimethylammonium acetylacetonate, benzyltriethylammonium acetylacetonate, tetramethylphosphonium acetylacetonate, tetraethylphosphonium acetylacetonate, tetrapropylphosphonium acetylacetonate, tetrabutylphosphonium acetylacetonate, benzyltrimethylphosphonium acetyl acetonate, benzyltriethylphosphonium acetylacetonate. Particular preference is given to using tetraethylammonium acetylacetonate and tetrabutylammonium acetylacetonate. It is of course also possible to use mixtures of such catalysts.

Additionally suitable as catalyst d) are aluminium, zirconium, titanium and/or boron alkoxides and/or aluminium, zirconium, titanium and/or boron esters.

Also suitable as catalysts are basic substances, for example guanidines and amidines and tertiary amines. Examples of these are tetramethylguanidine, diazabicycloundecene (DBU), diazabicyclononene (DBN), and diazabicyclooctane (DABCO).

As catalyst d) it is also possible to catalyse the urethane reaction using catalysts which have proved their worth within the field of PU technology, examples being organic Sn(IV), Sn(II), Zn and Bi compounds, or organometallic catalysts, for example dibutyltin dilaurate, tin octoate, zinc ethylhexanoate, bismuth neodecanoate, or tertiary amines, for example 1,4-diazabicyclo[2.2.2]octane. Catalysts of these kinds for urethane reactions are used in accordance with the invention, however, only in blends with other catalysts of the invention. Preference is given to using zinc ethylhexanoate.

As catalyst d) it is also possible to use a phosphorus-containing catalyst, preferably a phosphorus- and nitrogen-containing catalyst. Mixtures of two or more different catalysts may also be used here. Examples of suitable phosphorus-containing catalysts are substituted phosphonic diesters and diphosphonic diesters, preferably from the group consisting of acyclic phosphonic diesters, cyclic phosphonic diesters, acyclic diphosphonic diesters and cyclic diphosphonic diesters. Catalysts of these kinds are described in DE-A 102005045228, for example.

As catalyst d) it is also possible with preference to use an amine-blocked phosphoric ester and with particular preference amine-blocked ethylhexyl phosphate and amine-blocked phenyl phosphate. Examples of amines with which the phosphoric esters are blocked are especially tertiary amines, for example triethylamine. Particularly preferred for use for blocking the phosphoric esters are tertiary amines which exhibit high catalyst activity at curing temperatures of 100 to 160° C. Certain amine-blocked phosphoric acid catalysts are also available commercially (e.g. Nacure products from King Industries). An example of a particularly suitable catalyst is that based on an amine-blocked partial ester of phosphoric acid, under the designation Nacure 4167 from King Industries.

Also possible for use as catalyst d) are organic sulphonic acids in non-blocked or blocked form. A suitable sulphonic acid is in principle any organic sulphonic acid, preference being given to p-toluenesulphonic acid and dodecylbenzenesulphonic acid. For coating systems which crosslink thermally, i.e. above 100° C., these sulphonic acids, in accordance with the invention, may also be employed preferably in amine-neutralized form. Also possible for use in accordance with the invention are latent, non-ionogenic sulphonic acid derivatives which release sulphonic acids only at above 100° C., such as adducts of sulphonic acids with epoxide-containing components, for example, as described in DE-A 23 56768. Salts of trifluoromethanesulphonic acid (triflates) as well are suitable sulphonic acid-based catalysts.

Preferred for selection as catalysts d) are tetraethylammonium benzoate, tetrabutylammonium hydroxide, tetraethylammonium acetylacetonate, tetrabutylammonium acetylacetonate, dibutyltin dilaurate, zinc acetylacetonate, zinc ethylhexanoate.

The catalyst d) in the coating compositions of the invention may consist solely of the abovementioned alternatives, although any desired mixtures of the catalysts may also be used.

The coating composition of the invention may further comprise auxiliaries and/or additives e) that are known within coatings technology, such as stabilizers, including light stabilizers, catalysts, additional crosslinkers, fillers, pigments, flow control agents or rheological assistants, such as "sag control agents", for example, microgels or pyrogenic silicon dioxide or else nanoparticles, as described for example in EP 1204701 B1, in typical concentrations. Component e) may further comprise additional crosslinkers as known within coatings chemistry, which are used, for example, in the form of melamine resins, benzoguanamine resins, carbamate-functional components or blocked polyisocyanates. If necessary, inorganic or organic colour and/or effect pigments customary in coatings technology may also be incorporated in component e) of the coating compositions of the invention.

In one preferred embodiment the coating composition of the invention is a pigment-free system, i.e. a clearcoat system. Component e) in this case may be included in the coating composition of the invention preferably in an amount of 0.5 up to 8 weight percent, more preferably 1 to 6 weight percent, based on the sum of the components a), b), optionally c) and d).

In another preferred embodiment, the coating composition of the invention is a coloured coating system. Pigments and fillers as component e) may in this case be included in the coating composition of the invention in an amount from 10 to 200 weight percent, based on the sum of the components a), b), optionally c) and d).

The coating composition of the invention may further comprise organic solvents as component f). Suitable solvents are, for example, ketones, alcohols, esters, or aromatics.

Component f) is included in the coating composition of the invention preferably in amounts from 20 up to 150 weight percent, more preferably 30 to 60 weight percent, based on the sum of the components a), b), optionally c) and d).

The coating compositions of the invention are produced by mixing of the components described above. The mixing may take place by means of mixers known to the skilled person, for example batchwise in stirred containers, dissolvers, bead mills, roll mills, etc., or else continuously using static mixers, for example.

Another subject of the invention is the use of the alkoxysilane-functionalized, allophanate-containing coating compositions in paint compositions and adhesive compositions and metal-coating compositions.

Another subject of the invention is the use of the alkoxysilane-functionalized, allophanate-containing coating compositions in coating compositions and paint compositions for metal, glass, plastic, wood, MDF (Middle Density Fibreboards) or leather substrates or other heat-resistant substrates.

Another subject of the invention is the use of the alkoxysilane-functionalized, allophanate-containing coating compositions of the invention in adhesive compositions for bonds of metal, plastic, glass, wood, MDF or leather substrates or other heat-resistant substrates.

Likewise a subject of the invention are metal-coating compositions, more particularly for car bodies, motorcycles and pedal cycles, parts of buildings and household appliances, wood-coating compositions, MDF coatings, glass-coating compositions, leather-coating compositions and plastic-coating compositions.

The present invention is more particularly illustrated by the following non-limiting examples from which further features, embodiments, aspects and advantages of the present invention may be discerned.

EXAMPLES

Ingredients:
Vestanat® EP-UPMS: trimethoxysilylpropyl methylcarbamate (Evonik Resource Efficiency GmbH) Vestanat® IPDI: isophorone diisocyanate (Evonik Resource Efficiency GmbH)
Vestanat® TMDI: mixture of 2,2,4-trimethylhexamethylene diisocyanate (2,2,4-TMDI) and 2,4,4-trimethylhexamethylene diisocyanate (Evonik Resource Efficiency GmbH)
Vestanat® HT 2500/100: hexamethylene 1,6-diisocyanate, homopolymeric (isocyanurate type) (Evonik Resource Efficiency GmbH)
Vestanat® EP Cat 11 B: tetraethylammonium benzoate in butanol (Evonik Resource Efficiency GmbH)
Tegoglide® 410: lubricity and antiblocking additive based on a polyethersiloxane copolymer (Evonik Resource Efficiency GmbH)
Vestanat® EP-M60: linear, short-chain, silane-functionalized crosslinker (Evonik Resource Efficiency GmbH)
Vestanat® EP-M95: branched, short-chain silane-functionalized crosslinker (Evonik Resource Efficiency GmbH)
Vestanat® EP-M120: linear, long-chain silane-functionalized crosslinker (Evonik Resource Efficiency GmbH)
Setalux® 1760 VB-64: Polyacrylate polyol, Nuplex Resins B.V.
Tinuvin® 292: sterically hindered amine, light stabilizer; BASF SE
Tinuvin® 900: UV absorber; BASF SE
Preparation Example 1

Alkoxysilane-Functionalized, Allophanate-Containing Binder, Component 1a
340.2 g of Vestanat® EP-UPMS, 0.3 g of zinc(II) ethylhexanoate and 159.7 g of Vestanat® IPDI were charged to a three-necked flask with reflux condenser, blanketed with nitrogen and heated with stirring to 100° C. After heating for 20 hours, an NCO content of 1.4 wt % NCO was obtained. Then 10.84 g of butanol were added and the mixture was heated at 100° C. for an hour until an NCO content of <0.1 wt % NCO was reached. The product after cooling to room temperature is the alkoxysilane-functionalized, allophanate-containing binder, component 1a, as a clear liquid having a viscosity of 14.3 Pas (at 23° C.).

Example 2

Alkoxysilane-Functionalized, Allophanate-Containing Binder, Component 2a 474.6 g of Vestanat® EP-UPMS, 0.22 g of zinc(II) ethylhexanoate and 211.8 g of Vestanat® TMDI were charged to a three-necked flask with reflux condenser, blanketed with nitrogen and heated with stirring to 100° C. After heating for 24 hours, an NCO content of 0.8 wt % NCO was obtained. Then 10.35 g of butanol were added and the mixture was heated at 65° C. for three hours until an NCO content of <0.1 wt % NCO was reached. The product after cooling to room temperature is the alkoxysilane-functionalized, allophanate-containing binder, component 2a as a clear liquid having a viscosity of 1170 mPas (at 23° C.).

Comparative Example 3A

Alkoxysilane-Functionalized, Allophanate-Containing Binder, Component 3a (Comparative Example)

44.3 g of Vestanat® EP-UPMS, 0.01 g of zinc(II) ethylhexanoate and 35.7 g of Vestanat® HT 2500/100 were charged to a three-necked flask with reflux condenser, blanketed with nitrogen and heated with stirring to 100° C. until the NCO content of <0.1 wt % was reached. Then, with heating maintained, 20 g of butyl acetate were added in order to lower viscosity. The resulting alkoxysilane-functionalized, allophanate-containing binder, component 3a, is a clear liquid having a viscosity of 750 mPas (at 23° C.).

TABLE I

Composition of the inventive clearcoats and comparative examples (amounts in grams)

| | Item | I As per invention | II As per invention | III Comparison | IV Comparison | V Comparison | VI Comparison |
|---|---|---|---|---|---|---|---|
| 1 | Alkoxysilane-functionalized, allophanate-containing binder component 1a) | 26.36 | | | | | |
| 2 | Alkoxysilane-functionalized, allophanate-containing binder component 2a) | | 27.79 | | | | |
| 3 | Alkoxysilane-functionalized, allophanate-containing binder component 3a) (comparative) | | | 29.81 | | | |
| 4 | Comparative example: Vestanat® EP-M95 | | | | 26.79 | | |
| 5 | Comparative example: Vestanat® EP-M60 | | | | | 26 | |
| 6 | Comparative example: Vestanat® EP-M120 | | | | | | 53.2 |
| 7 | Setalux® 1760 VB-64 (64% form), component b) | 41.18 | 43.41 | 36.79 | 41.85 | 40.6 | 41.6 |
| 8 | Vestanat® EP-CAT 11 B component d) | 1.05 | 1.11 | 0.95 | 1.06 | 1.0 | 1.1 |
| 9 | TegoGlide® 410 (10% in butyl acetate) | 0.50 | 0.49 | 0.49 | 0.48 | 0.49 | 0.5 |
| 10 | Tinuvin® 292 | 0.27 | 0.28 | 0.23 | 0.27 | 0.26 | 0.27 |
| 11 | Tinuvin® 900 (8% in xylene) | 3.30 | 3.47 | 2.94 | 3.34 | 3.25 | 3.33 |
| 12 | Butyl acetate/xylene (1:1) | 27.34 | 23.45 | 27.20 | 26.21 | 28.4 | 0 |

Clearcoats

For the formulation of the inventive clearcoat materials and of the comparative examples, the components of the compositions represented in Table 1 were mixed with one another immediately prior to processing.

The viscosity of the formulations, determined as the flow time in the DIN 4 cup at 23° C., was approximately 20 seconds.

Table 2 sets out the potlives of compositions I-VI. The potlives were determined as follows: The liquid sample for determination (at least 70 ml) is introduced into a 100 ml glass vial and provided vertically with a metal pin; hanging at the end of the pin immersed in the sample is a circular metal plaque having a diameter of approximately 2 cm. The glass vial is provided with a perforated lid and the metal pin is clamped into the gelation time instrument (Techne Gelation Timer). The sample is now in a water tank set at room temperature (23° C.) (Lauda thermostat model BK2). The metal pin in the sample moves up and down in oscillation at a constant rhythm until the resistance of the sample is greater than the force of the gelation time instrument. In this case, the metal pin remains stationary; the sample is "gelled". The time which elapses between the start of the oscillating movement of the metal pin and the end thereof is reported on the display of the gelation instrument.

TABLE 2

Potlives of compositions I-VI

| Clearcoat system | Potlife (h) |
|---|---|
| I | 18.8 |
| II | 14.0 |
| III (Comparison) | 5.8 |
| IV (Comparative example) | 4.3 |
| V (Comparative example) | 4.0 |
| VI (Comparative example) | 2.0 |

From the potlives set out in Table 2 it is clearly evident that the inventive alkoxysilane-functionalized, allophanate-containing binders I-II have a much longer potlife than the Comparative Examples III-VI. From the prior art (Comparative Examples IV-VI) there was no expectation that the potlife would be prolonged by a multiple when using the inventive alkoxysilane-functionalized, allophanate-containing binders I-II.

The mechanical characteristics were determined by applying all of the coating materials to phosphatized steel panels (Chemetall Gardobond 26S/60/OC) with a 120 μm bar coater and curing them at 160° C. for 22 minutes.

TABLE 3

Film properties of compositions I-III after curing at 160° C. (22 min)

| Composition | I | II | III (Comparison) |
|---|---|---|---|
| Cross-cut | 0 | 0 | 2 |
| Pendulum hardness (König) [s] after 1 d | 188 | 165 | 184 |
| MEK test [ASTM D 4752] (Double rubs, 1 kg applied weight) | >150 | >150 | >150 |

The film properties of coatings I and II, which comprise the inventive alkoxysilane-functionalized, allophanate-containing binder components 1 and 2, exhibit improved adhesion (cross-cut) for approximately the same pendulum hardness and MEK resistance as Comparative Example III. In the case of formula III in particular, which contains the triply functionalized Comparative Example 3, the expectation, on the basis of the higher degree of crosslinking, would have been a greater hardness than the coatings I and II, which comprise the inventive alkoxysilane-functionalized, allophanate-containing binder components 1 and 2.

The invention claimed is:

1. An alkoxysilane-functionalized, allophanate-containing coating composition comprising
   a) as a binder component, 10-99 wt % of at least one reaction product of
   i) at least one monourethane i) containing alkoxysilane groups and of the formula 1

$R_n(OR^1)_{3-n}Si—R^2—NH—(C=O)—OR^3$     formula 1
   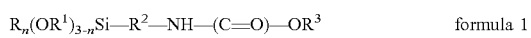

where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and
   ii) at least one diisocyanate ii),
   in a molar ratio of i) to ii) of from 3:1 to 1.5:1;
   b) 1-90 wt % of at least one other binder component, different from a),
   c) 0-50 wt % of at least one aromatic, aliphatic or cycloaliphatic polyisocyanate having an NCO functionality of at least 2,
   d) 0-5 wt % of at least one catalyst,
   where components a)-d) add up to 100 wt %,
   e) optionally auxiliaries and/or additives,
   f) optionally solvents.

2. The alkoxysilane-functionalized, allophanate-containing coating compositions according to claim 1, wherein R, $R^1$, $R^2$ and $R^3$ are at the same time or each independently methyl, ethyl, n-propyl, isopropyl, n-butyl, sec-butyl or tert-butyl.

3. The alkoxysilane-functionalized, allophanate-containing coating compositions according to claim 1, wherein n is 0, $R^1$ and $R^3$ are at the same time or each independently methyl or ethyl, and $R^2$ is at the same time or mutually independently methyl or propyl.

4. The alkoxysilane-functionalized, allophanate-containing coating compositions according to claim 1, wherein n is 0 and $R^2$ is methyl or propyl, and $R^1$ is methyl or ethyl and $R^3=R^1$.

5. The alkoxysilane-functionalized, allophanate-containing coating compositions according to claim 1, wherein n is 0, $R^1$ and $R^3$ are methyl and $R^2$ is propyl.

6. The alkoxysilane-functionalized, allophanate-containing coating compositions according to claim 1, wherein the diisocyanate ii) is selected from isophorone diisocyanate (IPDI), hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-dicyclohexylmethane diisocyanate (4,4'-H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), xylylene diisocyanate (MXDI), individually or in a mixture.

7. The alkoxysilane-functionalized, allophanate-containing coating compositions according to claim 1, wherein the binder b) is a hydroxyl-containing and/or amino-containing binder.

8. The alkoxysilane-functionalized, allophanate-containing coating compositions according to claim 1, wherein the binder b) is a hydroxyl-containing polyester, polyether, polyacrylate, polycarbonate and polyurethane having an OH number of 20 to 500 mg KOH/g and a mean molar mass of 250 to 6000 g/mol, alone or in a mixture.

9. The alkoxysilane-functionalized, allophanate-containing coating composition according to claim 1, wherein the binder b) is a hydroxyl-containing polyester or polyacrylate having an OH number of 50 to 250 mg KOH/g and a mean molecular weight of 500 to 6000 g/mol, alone or in a mixture.

10. The alkoxysilane-functionalized, allophanate-containing coating compositions according to claim 1, wherein the binder b) is at least one adduct of an isocyanatotrialkoxysilane and a mono- or polyhydric alcohol.

11. The alkoxysilane-functionalized, allophanate-containing coating compositions according to claim 1, wherein the binder b) is at least one derivative of hydroxyl-containing polyethers, polyesters, polycarbonatediols or polyacrylates with isocyanatopropyltrialkoxysilane, alone or in a mixture.

12. The alkoxysilane-functionalized, allophanate-containing coating compositions according to claim 1, wherein the binder b) is aminopropyltriethoxysilane, aminomethyltrimethoxysilane or aminomethyltriethoxysilane, alone or in a mixture.

13. The alkoxysilane-functionalized, allophanate-containing coating compositions according to claim 1, wherein the component c) is a polyisocyanate selected from isophorone diisocyanate (IPDI), hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-dicyclohexylmethane diisocyanate (4,4'-H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), xylylene diisocyanate (MXDI), individually or in a mixture.

14. The alkoxysilane-functionalized, allophanate-containing coating compositions according to claim 1, wherein the component c) is an isocyanurate, more particularly of IPDI and/or HDI.

15. The alkoxysilane-functionalized, allophanate-containing coating compositions according to claim 1, wherein the catalyst d) is selected from the group consisting of metal carboxylate, tertiary amine, amidine, guanidine, quaternary ammonium salts, tetraalkylammonium salts, quaternary phosphonium salts, metal acetylacetonates, quaternary ammonium acetylacetonates, quaternary phosphonium acetylacetonates, carboxylic acids, aluminium alkoxides, zirconium alkoxides, titanium alkoxides and/or boron alkoxides and/or esters thereof, phosphorus- and nitrogen-containing catalysts, sulphonic acids, alone or in a mixture.

16. The alkoxysilane-functionalized, allophanate-containing coating compositions according to claim 1, wherein the catalyst d) is selected from the group consisting of tetraethylammonium benzoate, tetrabutylammonium hydroxide, tetraethylammonium acetylacetonate, tetrabutylammonium acetylacetonate, dibutyltin dilaurate, zinc acetylacetonate and zinc ethylhexanoate.

17. The alkoxysilane-functionalized, allophanate-containing coating compositions according to claim 1, wherein the additive e) used is selected from the group consisting of solvents, stabilizers, light stabilizers, additional crosslinkers, fillers, pigments, flow control agents or rheological assistants, alone or in a mixture.

18. The process for producing the alkoxysilane-functionalized, allophanate-containing coating compositions according to claim 1 by mixing components a)-f).

19. A composition comprising the alkoxysilane-functionalized, allophanate-containing coating compositions according to claim 1, wherein the composition may be a paint compositions, adhesive compositions, sealant compositions or metal-coating compositions.

20. An alkoxysilane-functionalized, allophanate-containing coating compositions consisting of
a) as a binder component, 10-99 wt % of at least one reaction product of
i) at least one monourethane i) containing alkoxysilane groups and of the formula 1

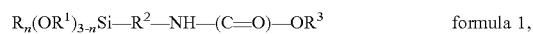

formula 1, where R, $R^1$, $R^2$ and $R^3$ are each independently hydrocarbyl radicals having 1-8 carbon atoms, which may be linear, branched or cyclic, or else may be integrated together to form a cyclic system, and n is 0-2,
and
ii) at least one diisocyanate ii),
in a molar ratio of i) to ii) of from 3:1 to 1.5:1;
b) 1-90 wt % of at least one other binder component, different from a),
c) 0-50 wt % of at least one aromatic, aliphatic or cycloaliphatic polyisocyanate having an NCO functionality of at least 2,
d) 0-5 wt % of at least one catalyst,
where components a)-d) add up to 100 wt %,
e) optionally auxiliaries and/or additives,
f) optionally solvents.

* * * * *